(12) United States Patent
Jimenez et al.

(10) Patent No.: US 11,701,518 B2
(45) Date of Patent: Jul. 18, 2023

(54) INTERNET OF MEDICAL THINGS THROUGH ULTRASONIC NETWORKING TECHNOLOGY

(71) Applicant: BioNET SONAR, Newton, MA (US)

(72) Inventors: Jorge Jimenez, Atlanta, GA (US); Tommaso Melodia, Newton, MA (US)

(73) Assignee: BioNET SONAR, Newton, MA (US)

( * ) Notice: Subject to any disclaimer, the term of this patent is extended or adjusted under 35 U.S.C. 154(b) by 335 days.

(21) Appl. No.: 17/044,682

(22) PCT Filed: Apr. 2, 2019

(86) PCT No.: PCT/US2019/025278
§ 371 (c)(1),
(2) Date: Oct. 1, 2020

(87) PCT Pub. No.: WO2019/195208
PCT Pub. Date: Oct. 10, 2019

(65) Prior Publication Data
US 2021/0146144 A1    May 20, 2021

Related U.S. Application Data

(60) Provisional application No. 62/651,503, filed on Apr. 2, 2018.

(51) Int. Cl.
*A61N 1/372* (2006.01)
*G16H 20/40* (2018.01)
(Continued)

(52) U.S. Cl.
CPC ..... *A61N 1/37217* (2013.01); *A61N 1/36135* (2013.01); *A61N 1/36564* (2013.01);
(Continued)

(58) Field of Classification Search
CPC .......... A61B 2560/0219; A61B 5/0022; A61B 5/0024; A61B 5/0028; A61B 5/0215; A61B 5/0245; A61B 5/076; A61B 5/686; A61B 5/6868; A61B 5/6869; A61B 5/7225; A61B 8/565; A61N 1/0534; A61N 1/36067; A61N 1/36082; A61N 1/36135; A61N 1/362; A61N 1/36564; A61N 1/37217;
(Continued)

(56) References Cited

U.S. PATENT DOCUMENTS

2002/0077673 A1   6/2002   Penner et al.
2006/0009818 A1   1/2006   von Arx et al.
(Continued)

OTHER PUBLICATIONS

PCT International Search Report and Written Opinion for PCT Application No. PCT/US2019/025278 dated Jun. 20, 2019 (9 pages).

*Primary Examiner* — George Manuel
(74) *Attorney, Agent, or Firm* — Eversheds Sutherland (US) LLP

(57) ABSTRACT

Wirelessly networked systems of implantable and non-implantable medical devices with networking protocols, software, and hardware that allow for communications and energy transfer between different the medical devices (free standing, implants and wearables) using ultrasonic waves. The networks and methods of use are used to construct cardiac pacing, deep brain stimulation, and neurostimulation networks based on ultrasonic wide band technology.

28 Claims, 10 Drawing Sheets

(51) Int. Cl.

| | | |
|---|---|---|
| *G16H 20/30* | (2018.01) | |
| *G16H 40/67* | (2018.01) | |
| *H04W 4/38* | (2018.01) | |
| *A61N 1/36* | (2006.01) | |
| *A61N 1/365* | (2006.01) | |
| *A61N 1/378* | (2006.01) | |
| *H04B 11/00* | (2006.01) | |
| *H04L 67/125* | (2022.01) | |
| *G16Y 40/50* | (2020.01) | |
| *G16Y 10/60* | (2020.01) | |
| *G16Y 20/40* | (2020.01) | |
| *A61N 1/05* | (2006.01) | |

(52) U.S. Cl.
CPC ....... *A61N 1/3787* (2013.01); *A61N 1/37288* (2013.01); *G16H 20/30* (2018.01); *G16H 20/40* (2018.01); *G16H 40/67* (2018.01); *H04B 11/00* (2013.01); *H04L 67/125* (2013.01); *H04W 4/38* (2018.02); *A61N 1/0534* (2013.01); *A61N 1/36067* (2013.01); *G16Y 10/60* (2020.01); *G16Y 20/40* (2020.01); *G16Y 40/50* (2020.01)

(58) Field of Classification Search
CPC .. A61N 1/37288; A61N 1/3787; G16H 20/00; G16H 20/30; G16H 20/40; G16H 40/63; G16H 40/67; G16H 50/20; G16Y 10/60; G16Y 20/40; G16Y 40/50; H04B 11/00; H04L 67/125; H04W 4/38
See application file for complete search history.

(56) References Cited

U.S. PATENT DOCUMENTS

| | | | |
|---|---|---|---|
| 2006/0252976 | A1 | 11/2006 | Rosero |
| 2007/0093875 | A1* | 4/2007 | Chavan ................ A61N 1/3787 607/46 |
| 2008/0021289 | A1 | 1/2008 | Zhang et al. |
| 2009/0082781 | A1 | 3/2009 | Tran et al. |
| 2010/0324378 | A1 | 12/2010 | Tran et al. |
| 2016/0157828 | A1* | 6/2016 | Sumi ...................... G01N 29/46 702/189 |
| 2016/0211924 | A1 | 7/2016 | Deng et al. |
| 2016/0235301 | A1 | 8/2016 | Melodia et al. |
| 2017/0367578 | A1 | 12/2017 | Melodia et al. |
| 2018/0000344 | A1* | 1/2018 | Melodia ................ H04W 84/18 |

* cited by examiner

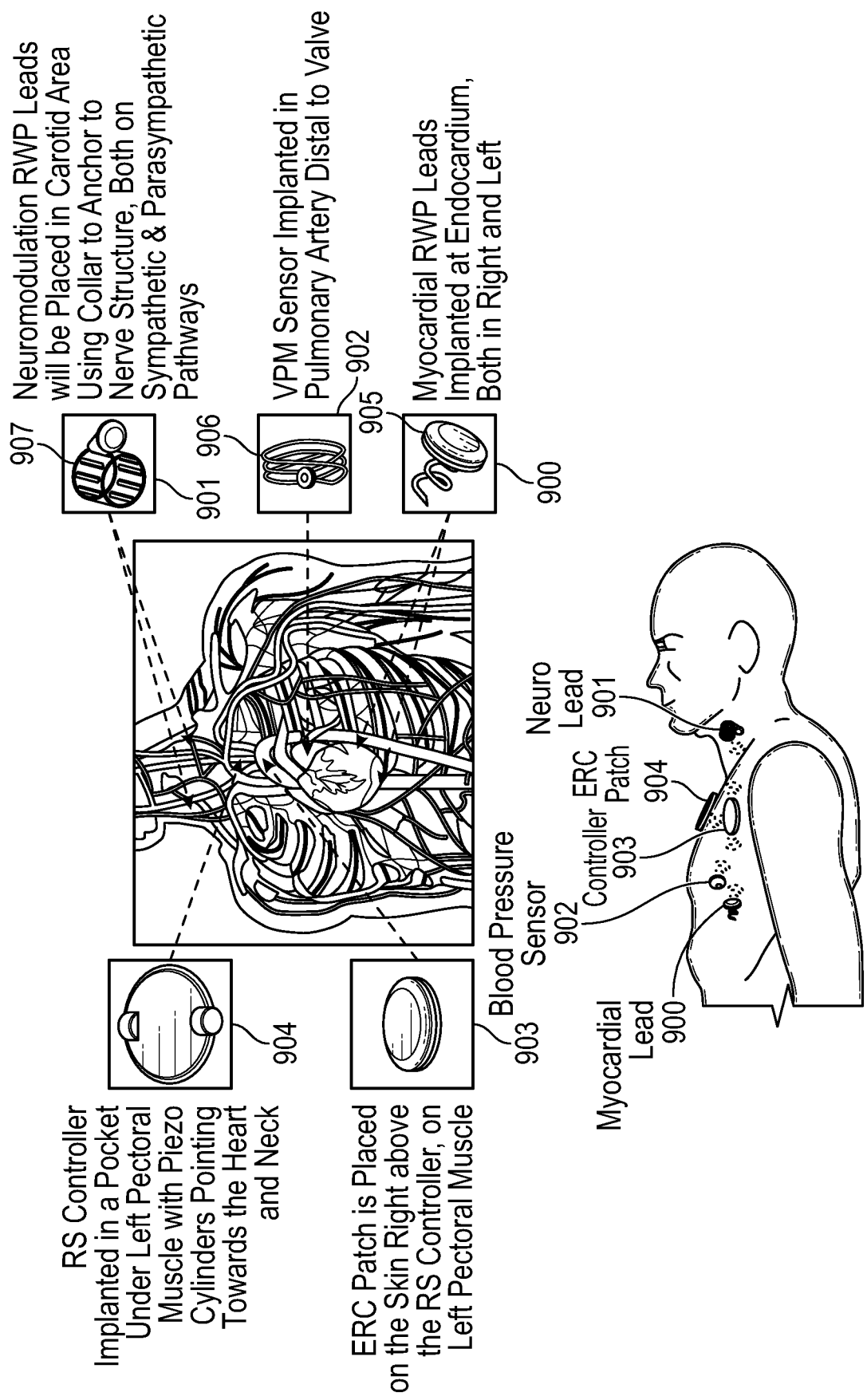

INTERNET OF MEDICAL THINGS THROUGH ULTRASONIC NETWORKING TECHNOLOGY

CROSS REFERENCES TO RELATED APPLICATIONS

This application claims the priority benefit of PCT/US2019/025278 filed on Apr. 2, 2019 which claims the priority benefit of U.S. Provisional Application No. 62/651,503, filed Apr. 2, 2018, which applications are incorporated herein by reference.

TECHNICAL FIELD

This invention relates to networking protocols, software, and hardware that allow for communications and energy transfer between different medical devices (free standing, implants and wearables) using ultrasonic waves.

BACKGROUND OF INVENTION

In the near future, wirelessly networked systems of implantable and non-implantable medical devices endowed with sensors and actuators will be the basis of many innovative, sometimes revolutionary therapies. However, radio-frequency (RF) electromagnetic waves, which are the physical basis of wireless technologies like Wi-Fi and Bluetooth, have limited penetration depth, low reliability, and high-energy consumption when propagating through biological tissues. Additionally, RF-based technologies are vulnerable to interference from other RF communication systems, and can be easily jammed or eavesdropped. The core technology on which this application is based uses ultrasonic waves for Ultrasound Wide Band (UsWB) communication, allowing for more reliable and energy efficient transmission of data and energy.

The medical field increasingly relies on sophisticated medical implants, wearables or freestanding equipment. Medical implants are becoming smaller, smarter, and connected. A growing percentage of implants already have data processing and wireless connectivity (for diagnostics, real-time continuous monitoring, or device re-configuration). Wirelessly networked systems of implantable medical devices endowed with sensors and actuators will be the basis of many innovative, sometimes revolutionary therapies. Existing and future applications of wireless technology to medical implantable (as well as wearable) devices will grow into a new market refer to as "The Internet of Medical Things" (IoMT). To enable this, wireless networking devices will need to be based on: (i) miniaturized elements for less invasive deployment; (ii) energy-efficient and reliable data transmission within the body; (iii) minimal power consumption and capabilities to recharge; (iv) secure remote monitoring and control of the implantable device from outside the body; (v) capabilities to process data in real-time; and (vi) re-programmability and coordination of network devices.

Radio-frequency (RF) electromagnetic waves, and specifically microwaves, which are the physical basis of commercial wireless technologies like Wi-Fi, Bluetooth, and Medical Implant Communication Systems (MICS) are heavily absorbed by biological tissues. As a consequence, (i) RF based transmission heats up tissues, which limits applications in delicate parts of the body such as the brain; (ii) signal absorption limits efficiency, thus requiring larger energy storage/batteries; (iii) tissues also significantly distort and delay RF signals, which causes data transmission to become less reliable; and (iv) absorption limits depth of signal penetration for data or energy transmission.

In contrast, ultrasonic transmission of data and energy does not suffer from the drawbacks since mechanical waves are not absorbed to the same extent in biological tissues. Therefore, ultrasonic communication would better enable the creation of implantable Internet of Medical Things (IoMT) communicating devices with and within the human body. The specific communication techniques, hardware, software and protocols described here provide details on how to create an Ultrasonic Wide Band (UsWB) network of medical devices.

Some of the most advanced medical technologies rely on RF based technologies to communicate outside the human body from subcutaneous implants, but still rely on wired/cables connections to communicate to different areas of the body. Cardiac pacemakers and neurostimulation systems are good examples of such technologies where wires/leads are used to send data and energy to other locations in the body from subcutaneous devices. Several complications such as infections, lead failure, pain due to tethering of wires, heart valve malfunction, among others have been associated with the tunneling and chronic implant of such wires and/or leads. Therefore, it would be beneficial to have a wireless network of implantable devices for both intra-corporeal and extra-corporeal communication and/or energy transfer to minimize such complications. The UsWB platform allows for intelligent wireless networks for bi-ventricular pacing, deep brain stimulation, and several other applications that may also include remote monitoring capabilities. These networks will reduce mortality/complications in patients with different diseases while reducing healthcare costs associated with in-hospital visits.

SUMMARY OF THE INVENTION

Embodiments described herein provide devices, systems, communication protocols and wireless links, and methods for creating wireless networks of devices inside and outside the human body in order to treat patients without the complexity and complications associated with the use of implanted wired systems.

Many different networks of implantable devices to treat different etiologies maybe designed using the UsWB technology to communicate and/or transmit energy. Recognizing that the versatility of the platform technology is significantly higher than a single medical application, a dual-level modular approach is the basis for the different networks. For the first level, implantable devices are designed and/or built following a modular approach (device level), by combining different functional units with the primary ultrasonic IoMT platform. Second, networked medical application are built by combining the functionalities of different implantable devices working in a coordinated fashion (network level). Such a modular approach reduces hardware changes associated with different applications by focusing on software/firmware changes on versatile hardware.

At the device level, the core building block unit, the "IoMT platform" is combined with functional units to define a functional network node. Typical functional nodes used as building blocks of medical devices (implants or wearables) are: (i) sensing node; (ii) actuation node; (iii) control node; and (iv) energy transfer/gateway node, or combinations thereof. In exemplary embodiments, a single medical device can be constructed with a single functional node, whereas in other exemplary embodiments a medical device may be defined by a plurality of functional nodes. Therefore, networked elements include both devices and/or functional nodes. A network under this definition can thus be described as a network of functional nodes or a network of medical devices, interchangeably, depending on the desired representation of the components.

At the network level, the re-programmability of each functional node (with perhaps limited hardware tuning), as well as their interconnection enabled by the common ultrasonic networking protocol stack, is used to create different networked applications based on interactions between similar functional nodes. Therefore, different networks of these functional nodes will allow for different therapies in different parts of the body as a limited breadth of actuation and monitoring functions with varying programming control can treat different pathological conditions.

A vast number of different networks of medical "things" may be created to treat or monitor patients with different pathologies. These may be simply a combination of a controller or gateway nodes with a sensor node for remote monitoring of patient health by measuring physiological parameters (e.g., a blood pressure sensor to monitor hypertension); or, can be as complex as networks with multiple and diverse actuators, sensors, control and gateway nodes that can be used to jointly monitor and treat a condition remotely. Most medical network applications can be grouped into two major categories: (i) intelligent monitoring and pacing networks; and (ii) monitoring and drug delivery control networks.

Several embodiments of implantable and non-implantable nodes have been designed for different applications such as: deep brain stimulation, cardiac pacing, cochlear/auditory device recharging and reprograming, intra-ocular pressure monitoring for glaucoma, wireless neonatal monitoring, brain neuro-stimulation, peripheral nerve stimulation, spinal cord stimulation, gastric pacing, artificial limb control, ventricular assist device control and recharging, monitoring or orthopedic implants, monitoring or artificial heart valves, glucose monitoring and insulin pump control, and controlled drug delivery among others.

In a preferred embodiment of the invention, network functional nodes are used for cardiac pacing and neurostimulation by themselves and/or in combination to treat different etiologies of human disease. In one exemplary embodiment a network of functional nodes is used to combine cardiac resynchronization therapy with neurostimulation in order to reduce mortality and improve quality of life in heart failure patients. In another exemplary embodiment a wireless bi-ventricular pacing network of functional nodes is used to reduce cardiac lead-based complications while monitoring cardiac pressure. In a further exemplary embodiment a network of functional nodes is used for wireless deep brain stimulation (DBS) in Parkinson's disease patients to reduce tremors and improve their quality of life. These networks all have in common functional pacing/stimulation nodes, sensor nodes, implantable control nodes, and external communication/recharging gateway nodes.

BRIEF DESCRIPTION OF THE DRAWINGS

Figure 1:
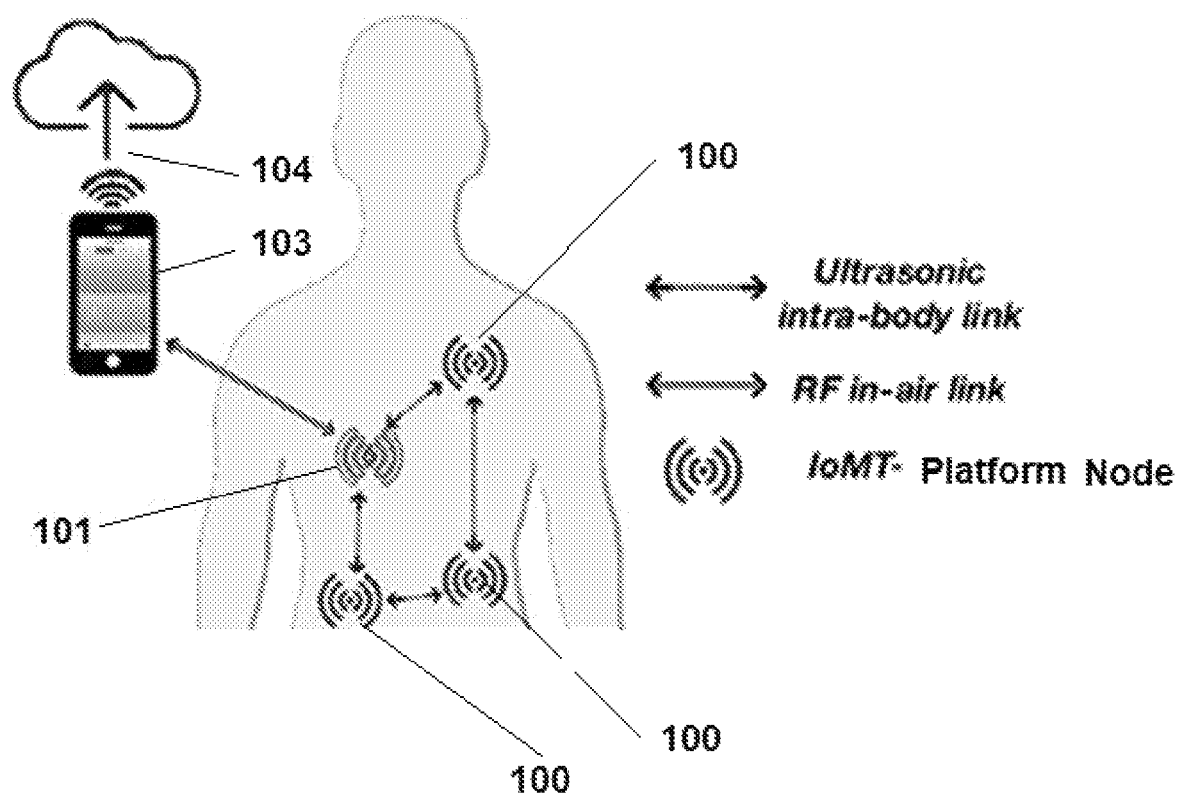

Having thus described various embodiments of the present invention in general terms, reference will now be made to the accompanying drawings, which are not necessarily drawn to scale, and wherein:

FIG. 1 shows the different types of communication links used in the modular networks for both implantable and non-implantable components of the network.

Figure 2:
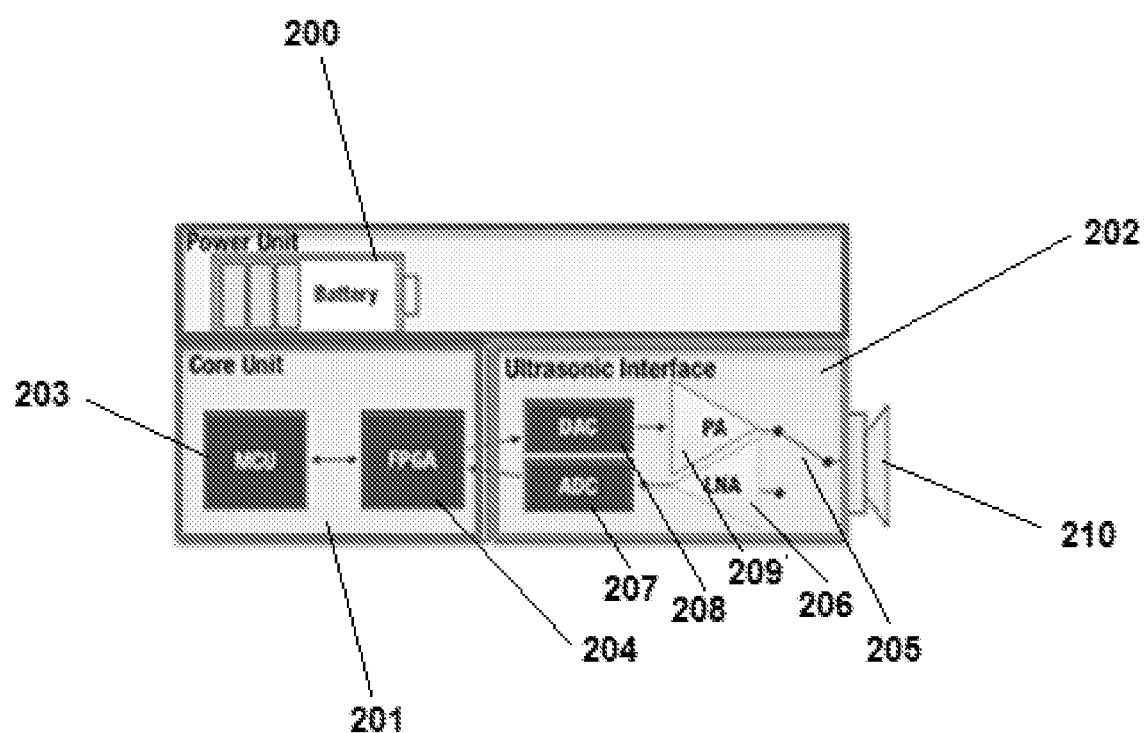

FIG. 2 Block diagram of the principal components of the IoMT platform. Three main block constitute the platform itself: i) Energy Storage unit, ii) Core Units, and iii) Ultrasonic interphase.

Figure 3:
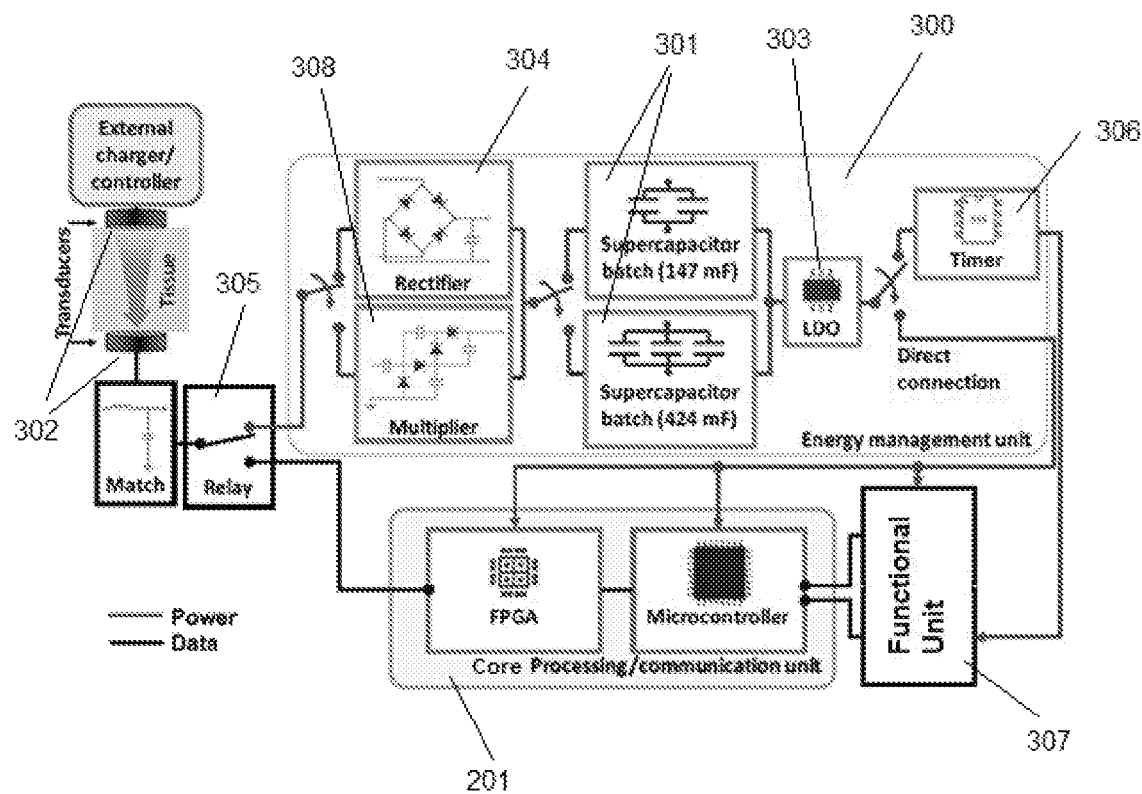

FIG. 3 Block diagram of a functional node that can be recharged wirelessly using ultrasonic waves. The addition of a functional unit to the basic IoMT platform structure constitutes a functional node. The energy management unit includes energy harvesting components and energy storage elements. The embodiment described in this diagram also uses a capacitor bank as energy storage for improved safety.

Figure 4:
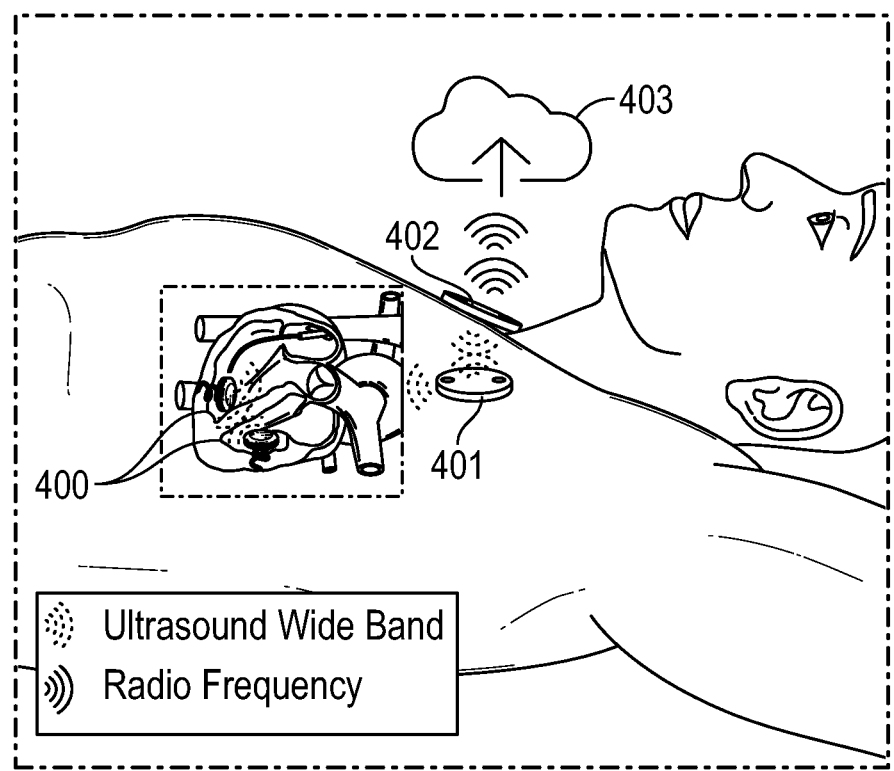

FIG. 4 Diagram of the different nodes/devices that constitute a wireless bi-ventricular pacing network enabled through ultrasonic communication and energy transmission.

Figure 5:
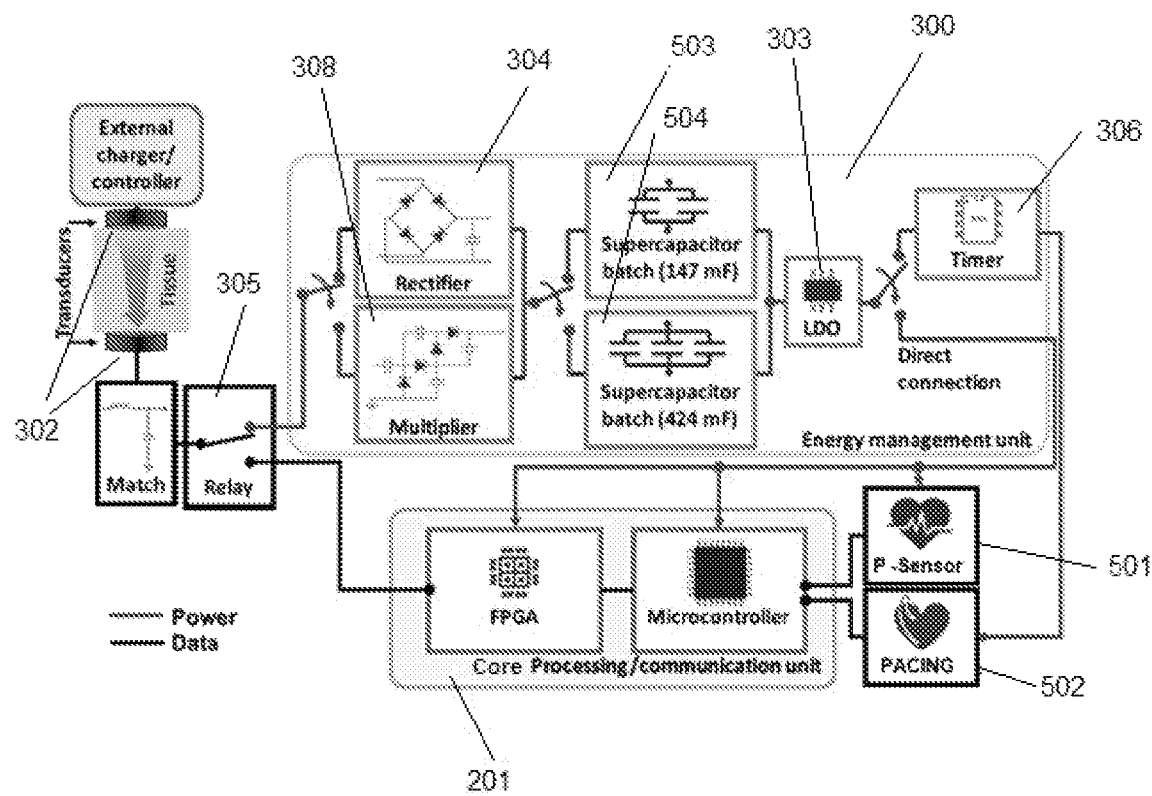

FIG. 5 Block diagram of the reprogrammable wireless pacing (RWP) nodes with vascular pressure monitoring. The components of the RWP nodes are similar to those of the generic IoMT platform with the addition of two functional units, a pressure sensor unit and an electric sensor/pacing unit. The RWP nodes are recharged using ultrasonic waves and therefore include the energy management unit with harvesting capabilities.

Figure 6:
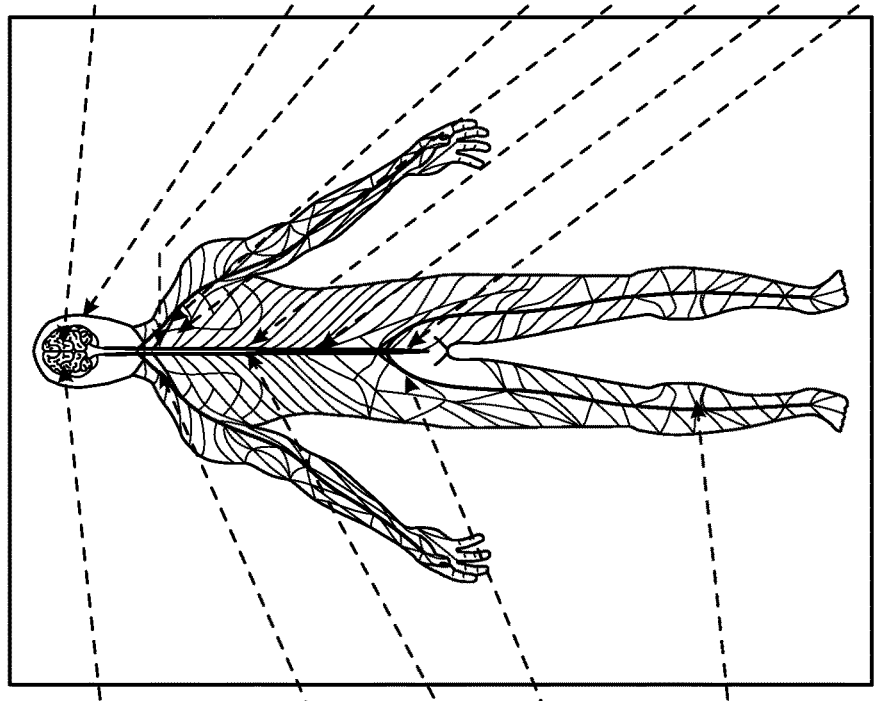

FIG. 6 Diagram showing different types of treatments using neurostimulation referenced to a specific stimulation site.

Figure 7:
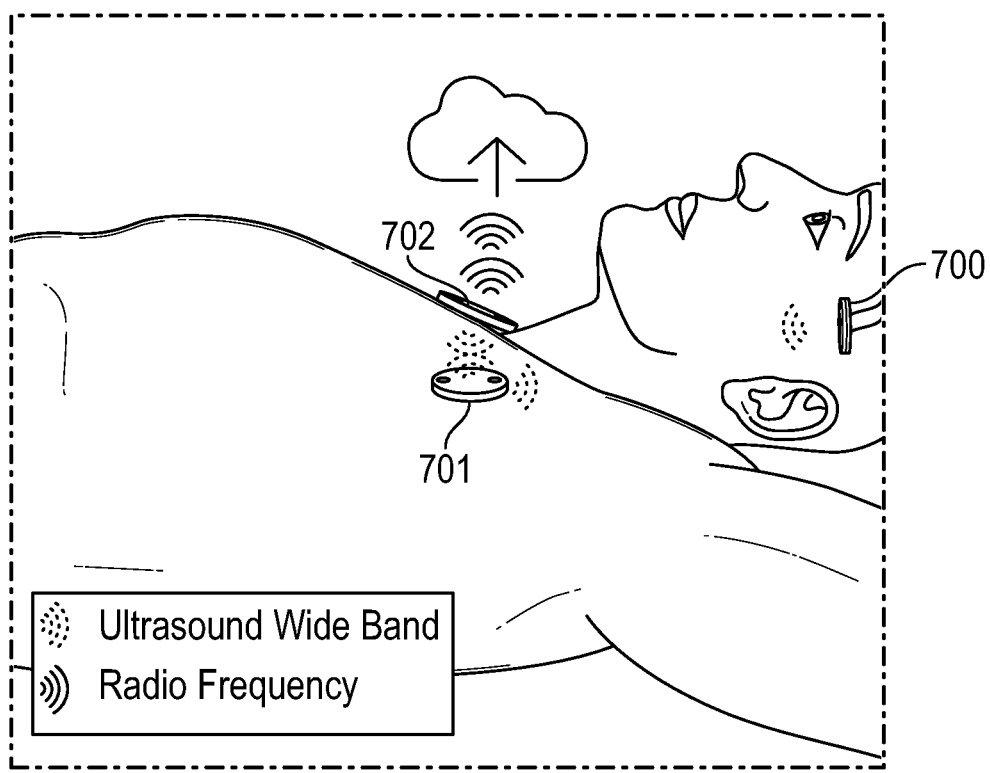

FIG. 7 Diagram of the different nodes/devices that constitute a wireless deep brain stimulation network enabled through ultrasonic communication and energy transmission.

Figure 8:
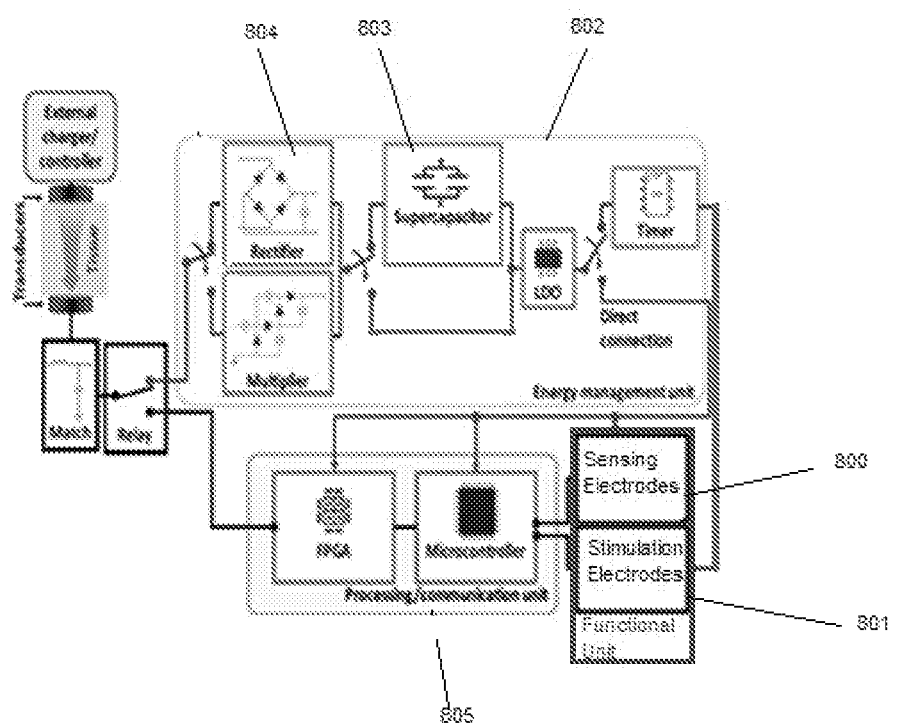

FIG. 8 Block diagram of a reprogrammable stimulation RSN node. The components of the RSN node are similar to those of the generic IoMT platform with the addition of two functional units, an electrical sensor unit and stimulation unit for multi-contact stimulation. The RSN node are recharged using ultrasonic waves and therefore include the energy management unit with harvesting capabilities.

FIG. 9 Diagram of the different nodes/devices that constitute a wireless neuromodulation/CRT network with vascular pressure monitoring capabilities for the treatment of heart failure patients.

FIG. 10 Block diagram of: A) Reprogrammable cardiac wireless pacing node and B) vascular pressure monitoring node, for a wireless neuromodulation/pacing network with vascular pressure monitoring capabilities.

DETAILED DESCRIPTION OF THE INVENTION

Embodiments of the present invention now will be described more fully hereinafter with reference to the accompanying drawings, in which some, but not all, embodiments of the inventions are shown. Indeed, the invention may be embodied in many different forms and should not be construed as limited to the embodiments set forth herein; rather, these embodiments are provided so that this disclosure will be thorough and complete, and will fully convey the scope of the invention to those skilled in the art. Like reference numbers refer to like elements throughout. The singular forms "a," "an," and "the" can refer to plural instances unless the context clearly dictates otherwise or unless explicitly stated.

The invention provides a wireless medical device network comprising: a plurality of networked elements, wherein at least two of these elements communicate with each other by sending or receiving data using ultrasonic waves. In embodiments, the ultrasonic wave is a pulsed wave. In embodiments, the ultrasonic wave is a continuous wave.

The invention provides a wireless medical device network comprising: a plurality of networked elements, wherein data is encoded in the frequency domain of the ultrasonic wave. In embodiments, data is encoded in the phase domain of the ultrasonic wave. In embodiments, data is encoded in the amplitude domain of the ultrasonic wave.

The invention provides a wireless medical device network comprising: a plurality of networked elements, wherein data is encoded in the relative position of ultrasound pulses with respect to a reference. In embodiments, data is encoded using a time-hopping scheme in the ultrasonic pulses. In embodiments, a single bit of data is encoded in a single ultrasonic pulse. In embodiments, a single bit of data is encoded in multiple ultrasonic pulses.

The invention provides a wireless medical device network comprising: a plurality of networked elements, wherein the ultrasonic wave is generate by a unidirectional ultrasonic transducer. In embodiments, the ultrasonic wave is generate by a multidirectional ultrasonic transducer. In embodiments, at least one network element is implanted within the human body. In embodiments, at least one network element is wirelessly recharged using ultrasonic waves.

The invention provides a cardiac medical device wireless network comprising: a plurality of networked elements, wherein at least one element is an implanted device; and, wherein at least two of these elements communicate with each other by sending or receiving data using ultrasonic waves. In embodiments, at least one implanted device is used for pacing of a heart chamber; wherein at least one implanted control element is used to control a pacing element. In embodiments, at least one implanted control element is used to wirelessly recharge a pacing element using ultrasonic waves.

The invention provides a wireless medical device network comprising: a plurality of networked elements, wherein at least one of the implanted elements has the capacity to measure blood pressure. In embodiments, at least one of the elements can communicate wirelessly to the internet.

The invention provides a cardiac medical device wireless network comprising: a plurality of networked elements. In embodiments, the ultrasonic wave is a pulsed wave. In embodiments, a single bit of data is encoded in multiple ultrasonic pulses.

The invention provides a neurostimulation medical device wireless network comprising: a plurality of networked elements, wherein at least one element stimulates or modulates the nervous system. In embodiments, at least two of these elements communicate with each other by sending or receiving data using ultrasonic waves. In embodiments, at least one element is an implanted device. In embodiments, at least one device is implanted within the brain. In embodiments, at least one element is used for deep brain stimulation therapy. In embodiments, the ultrasonic wave is a pulsed wave. In embodiments, at least one device is connected to the peripheral nervous system.

The invention provides a neurostimulation medical device wireless network comprising: a plurality of networked elements, wherein the ultrasonic wave is a pulsed wave. In embodiments, at least one network element can increase or decrease cardiac function.

Radio-frequency (RF) electromagnetic waves, and specifically microwaves, are heavily absorbed by biological tissues fluid and other solids. As a consequence, (i) RF based transmission heats up tissues, which limits applications in delicate parts of the body such as the brain; (ii) signal absorption limits efficiency, thus requiring larger energy storage/batteries; (iii) tissues also significantly distort and delay RF signals, which causes data transmission to become less reliable; and (iv) absorption limits depth of signal penetration for data or energy transmission. In contrast, ultrasonic transmission of data and energy does not suffer from the drawbacks, since mechanical waves are not absorbed to the same extent in biological tissues.

As shown in FIG. 1, in a preferred embodiment the nodes of the intra-body network 100 communicate/link and/or send energy using ultrasonic waves while the nodes external to the body 101 can use RF based communication links to communicate with other external elements. In exemplary embodiments, the extracorporeal nodes can still use ultrasonic waves to communicate through the air when such a link is desired. Using these external links the intra-corporeal network can communicate to the internet of things, the general internet, physical computers/servers/equipment, or the cloud. External communication links allow data to be stored or monitored remotely. In preferred embodiments, the intra-body network can also be controlled or re-programmed remotely using these data links. In exemplary embodiments, the data of one or more patients received from this networks can be processed using standard or artificial intelligence algorithms to improve patient treatment for the general patient population or provide patient centric tailored treatment.

Many different networks of implantable devices to treat different etiologies may be designed using the UsWB technology to communicate and/or transmit energy. There are several common types of implants that can be used in distinct networks to treat different forms of disease. Therefore, to reduce development timelines/cost and regulatory burden, proven modular hardware elements from one network are used in another to enable another applications. Therefore, a dual-level modular approach is the basis for the different networks. For the first level, implantable devices are designed and/or built following a modular approach (device level), by combining different functional units with the primary ultrasonic IoMT platform. Second, a networked medical application is built by combining the functionalities of different devices working in a coordinated fashion (network level).

At the device level, the core building block, "IoMT platform", is used to create implants (and wearables) with specific functions by adding one or several functional units. Devices configured in this way are defined as a functional node. Typical functional nodes to used as building blocks of medical devices (implants or wearables are (i) sensing nodes; (ii) actuation nodes; (iii) control nodes; and/or (iv) energy transfer/gateway nodes.

As shown in FIG. 2, in a preferred embodiment the basic IoMT platform is constructed from three primary units, although in some exemplary embodiments all these units may not be present. These primary units are: (i) power unit 200, (ii) core unit 201, and a (iii) ultrasonic interface 202. In exemplary embodiments, the different components that make up these units above can be implemented in several circuit boards or electronic components. In some preferred embodiments, the IoMT is implemented in a multi-layer board that may contain all the units named above. In a further embodiment System-on-Chip (SoC) solutions will be used to integrate different hardware components of the IoMT platform inside a single chip.

As shown in FIG. 3, in a preferred embodiment, the power unit will include both an energy harvester and/or energy storage/buffer when required, defining an energy management unit (EMU) 300. Storage/buffer 301 can take the form of a battery (standard or rechargeable), a capacitor, or an array of capacitors or any other voltage storing electronic element. The selection of the type of energy storage will depend on size requirements, life expectancy, and the risks associated with battery replacement.

In a preferred embodiment, the EMU 300 includes an ultrasonic energy harvester that is used to receive ultrasonic waves from other node/nodes of the network and transform these waves into energy that can be used to power the receiving node. In this embodiment, different network nodes can received and/or send energy using ultrasonic waves. When sending energy, the EMU in combination with other units of the node can take alternating current (AC) signal, or a square wave, generated at ultrasonic frequencies (>20 kHz) to drive an electro-acoustic transducer 302 that transmits power to another node. The transducer converts the electrical waveform to mechanical waves. When receiving ultrasonic energy, an acousto-electric transducer transforms the mechanical excitation back into an electrical AC signal. In an exemplary embodiment, the EMU can also contain a rectifier and/or a multiplier circuit, and a low dropout (LDO) regulator 303 to limit the voltage delivered. The storage components (battery, capacitors, etc) 301 need a direct current (DC) voltage to be recharged, which requires the presence of the rectifier 304 whose role is to generate a DC voltage from an oscillating input. The core unit 201 helps control part of the energy harvesting system as well as an ultrasonic transceiver for data communication. When utilizing the same transducer to send/receive data and energy, a switch 305 is used to change from an energy sending/receiving phase to a communication phase in the operation cycle of the transducer. During the first phase, the platform is remotely recharged via ultrasonic transcutaneous energy transfer (UTET). During the second phase, the harvested energy is used to power the circuitry to activate processing, sensing, actuation, and communication functions. In specific embodiments, the platform actually sends energy during the first phase and second phases, such as in the case of a IoMT platform as part of a control node. The phase switch can work using prescribed times from a timer, or can be controlled by the core unit elements 201. In exemplary embodiments of the energy harvesting system, different transducers are used to send/receive data and energy, thus not requiring the switch controlled 305 dual phase cycle described above. Additional elements as a secondary timer 306 to control switching between data processing in the core unit 201 and powering the functional unit 307 of the functional node, can be included, to improve energy efficiency. A multiplier circuit 308 can also be included to help with signal processing and/or amplification.

The core unit 201 may include a stand-alone microcontroller, or a combination of a microcontroller (MCU) 203 and reconfigurable hardware, such as a field-programmable gate array (FPGA) 204; or even a stand-alone FPGA. In exemplary embodiments, other type of reconfigurable hardware can be used like application-specific integrated circuits (ASICs). Depending on the processing requirements and desired size, any of these options may be used. In a preferred embodiment where the MCU and FPGA are combined, their combination results in hardware and software reconfigurability with very small packaging and low energy consumption. The miniaturized FPGA 204 hosts the physical PHY layer communication functionalities. The MCU 203 is in charge of data processing and of executing software-defined functionalities to implement flexible and reconfigurable upper-layer protocols. These upper-layer protocols may include in some embodiments non-time critical MAC functionalities, network, transport and application, among others. In the exemplary embodiment, the software is split between FPGA 204 and MCU 203. The FPGA 204 implements the PHY layer communication functionalities, as well as interfaces to connect the FPGA 204 chip with the MCU 203 and the peripherals. In the exemplary embodiment the MCU software design is based on the pTasker real-time operating system (RTOS) that supports timers and interrupts for sensing and transmitting data and executes the upper layer networking protocols. The IoMT platform software framework also provides a set of primitive functions to be used as building blocks to develop specific data processing applications. To someone skilled in the art is it understandable that all software could be implement in any of the components that may be included in the core unit dependent on the algorithm design and processing requirements. In the preferred embodiments the functionalities are implemented to minimize the system energy consumption by leveraging pTasker primitives to access different power states. Specifically, an energy management module is able to (i) adjust at runtime the core clock frequency and low-power mode according to application requirements, and (ii) implement automatic wake-up functionalities. This implementation will allow the MCU current consumption to be reduced from its values in a RUN state down to lesser values in very-low-leakage-state, with intermediate states that trade current consumption for wake-up time.

The ultrasonic interface 202 in preferred embodiments will be common to different types of nodes in the same network, thus enabling internetworking; depending on the power unit type, it may also have an interface for energy harvesting. The ultrasonic interface enables wireless connectivity and consists of a receiver (Rx) and a transmitter (Tx) chain. Depending on the number of ultrasonic transducers, the Rx and Tx can work in parallel or may need to be switched 205 to work in series in controlled cycles over time. The Rx chain includes a low-noise amplifier (LNA) 206 and an analog-to-digital converter (ADC) 207 to amplify and digital-convert received signals, while the Tx chain embeds a digital-to-analog converter (DAC) and a power amplifier (PA) to analog-convert and amplify the digital waveform before transmission.

The ultrasonic interface can use a single or a plurality of transducers. When a single ultrasonic transducer is used to operate several send/receive cycles, these cycles will be gated in time. In some embodiments both energy and data could be send in the same acoustic signal, although with limitation in the data transmission rate. In exemplary embodiments, multiple transducers can to send and or receive different signals. In exemplary embodiments, different transducers can be used to separate the energy and data transmission functions or different transducers can be used to send signals in different directions. In exemplary embodiments, unidirectional transducers may suffice, but when directional tolerances are important so that the beam reaches efficiently another node, a multidirectional or omni-directional transducer should be used. Directionality of the transducers is achieved by an array design (array of unidirectional piezos pointed in different directions) or by the shape of the ultrasound emitting element or piezo (cylindrical, semi-spherical, spherical, etc). Both, piezoelectric ultrasonic transducers (crystal, ceramic, polymers, organics and composites) or capacitive ultrasonic transducers can be used in the ultrasonic interphase unit. In exemplary embodiments, capacitive transducers include those micro-machined using MEMs technologies and well as others which use more traditional manufacturing methods.

There are several exemplary embodiments that describe the ultrasonic waveforms used to send or received energy and/or data using UsWB. In some embodiments continuous ultrasound waves can be used while in others pulsed ultrasound waves may be preferred. In preferred embodiments using pulsed ultrasonic waves, discrete digitally modulated pulses of ultrasound are emitted from the transducer (discrete ultrasound wave pulse packages). In embodiments where data is sent through continuous waves, data can be encoded in the frequency or phase (frequency shift keying or phase shift keying) or amplitude domain (amplitude shift keying) or in a combination (quadrature amplitude modulation). In other embodiments data can be encoded in the relative position of ultrasound pulses with respect to a reference (pulse position modulation). When using pulsed ultrasound waves, data can be encoded in the frequency or amplitude domain, or in the relative positions of pulses in the ultrasonic wave. In a preferred embodiments, a time-hopping scheme is used to encode the data in the ultrasonic pulses. In some exemplary embodiments each bit of data can be encoded in a single pulse, while in preferred embodiments a single bit can be encoded within the signal structure of multiple pulses. In certain embodiments each bit can be represented with multiple pulses whose polarity or position can be modulated following a binary spreading code. The spreading code can be obtained through a pseudo-random generator, or it can follow a known and pre-defined pattern.

The core building block, the IoMT platform, can be combined with a functional unit 307 to create a functional node as described above. Possible functional units may have the largest range of variability and will determine the nature of the node. For example, for control nodes, the specification in its processing (core unit) and communication elements (ultrasonic interface) can define its function completely. In contrast, for energy transfer/gateway node the specific data interface with the external environment (e.g., WiFi, Bluetooth) and the type of energy transfer interface will define its range and specific function. In some embodiments, sensing nodes or actuation nodes (e.g., pacers) may tend to have a simple microcontroller as core unit; whereas control nodes and energy transfer/gateway nodes may require a more reconfigurable hardware so the same unit can be used in several different types of networks with very limited changes to hardware. Therefore, a large variability of component architecture can be used in different functional nodes depending on specification.

For sensing nodes, the specific physical sensor (electrical, acoustic, EKG, pressure, temperature, voltage/current, flow, chemical, Gas, Ph+ sensor, photosensor, accelerometer, etc) will define the functionality. Further, a specific sensing node can find many different medical applications in different parts of the body. For example, a pressure sensor can be used in cardiovascular (heart failure, Hypertension), ophthalmological (glaucoma), and spine (disk compression) applications, among others.

In some applications sensors nodes may be used in wearables or outside the body to create wireless network links through the air in environments where sensing of the human body is required and RF based links are not possible or not preferable. In a particular embodiment of UsWB transmission through the air, in the nursery or neonatal intensive care unit wired connections to sensors on the child's body or surrounding environment may be exchanges for wireless UsWB links to diminish concerns of having a high density RF environment surrounding a neonate or young child. This link can interface with an external control gateway to send data to a computer or the internet.

Actuation functional units also present a large range of variation, but in general for the human body the primary expected actuators are (i) mechanical/artificial limbs/prosthesis, (ii) electro stimulation/pacing, (iii) cameras, (iv) acoustic, and (v) drug delivery/pumps. Many applications may work in absence of a sensor node like when using a control or gateway node to recharge and/or reprogram and/or adjust a cochlear implant or auditory support device. In such an embodiment, the controller or gateway node may be located or embedded in an acoustic friendly environment like a gel pillow to recharge the auditory device when the patient is at rest, or as required.

Although there is a large range of possibilities and scopes, it should also be understood that the nervous system and the heart work within a very similar electro-potential range. Therefore, reprogrammable-pacing/stimulation actuation functional units for pacing the myocardium, the brain or nerves, can have in many cases identical/similar electronics, with differences mostly associated to casing, software, and anchoring elements. Therefore, exemplary embodiments of pacing/stimulation actuation functional unit may generate many types of functional nodes for several parts of the body for heart, brain, and nerve stimulation. Exemplary embodiments of this functional nodes also includes pacing of the gastric system (stomach, intestine) that is accomplished using a similar electro-potential pacing actuation node. Increased energy capacity for pacing may also allow for skeletomuscular stimulation or prosthesis control.

The preferred embodiment of treatment specific modular networks is associated to cardiovascular disease and neuro-stimulation/neuromodulation. In these networks implantable pacing or stimulation nodes may be controlled and powered/recharged by an implantable control node, that itself can be controlled, recharged and linked to an external network using an energy transfer/gateway node. In some simpler embodiments the pacing or stimulation nodes can be recharged and controlled directly by the energy transfer/gateway node in absence of the implanted control node.

In a primary embodiment of UsWB enabled pacing networks, ultrasonic energy transfer and UsWB communication technologies can be used to reduce complications associated with wired pacing leads (infection, lead failure, pain, etc), reduce battery exchange rates, and hospital visits through remote monitoring in patients that need single chamber or multi-chamber cardiac pacing. A cardiac pacing network to pace a single chamber of the heart or multiple chambers can be constructed from pacing functional nodes, a control node and an energy transfer/gateway node. This network may also include cardiac pressure sensing within the pacing node or as an independent pressure-sensing node. The exemplary embodiments for this network include single ventricle pacing or bi-ventricular pacing, although other applications may include or be limited to atrial pacing of a single or both atria.

In a preferred embodiment for a bi-ventricular pacing UsWB network, three different types of functional nodes are defied as shown in FIG. 4: (1) reprogrammable wireless pacing (RWP) nodes with vascular pressure monitoring 400, (2) rechargeable system (RS) control 401 node, and (3) external recharging and communications (ERC) node 402. All the elements in this network communicate with each other through proprietary Ultrasonic Wide Band (UsWB) technology. The RWP nodes and the RS control node are wirelessly recharged using ultrasonic energy transmission. UsWB platform is capable of sending energy and data via ultrasonic waves through tissue, bone, and fluids at penetration depths significantly higher than RF waves (up to 30 cm depth) and with better reliability (bit error rates better than $10^{-6}$). Since increasing energy efficiency results in reduced energy storage requirements, UsWB also enables miniaturization of medical devices. The RWP nodes 400 are implanted using minimally invasive (catheter based endovascular methods) in both ventricles, the RS controller 401 is implanted in a subcutaneous pocket in the chest of the patient, and the ERC node 402 is a wearable which is in contract with the skin. The ERC node 402 is removable and in preferred embodiments is attached to the skin using a glued patch. The contract area between the ERC node casing and the skin has ultrasonic coupling material.

As shown in FIG. 5. The components of the RWP nodes are similar to those of the generic functional node described in FIG. 3 with the addition of two functional units, a pressure sensor 501 and an electric sensor and pacing unit 502. The RWP nodes are recharged using ultrasonic waves and therefore include the EMU 300 with harvesting capabilities. RWP nodes 400 have reprogrammable electronic hardware that can be easily adapted to pace cardiac muscle and/or other structures. RPWs are anchored to the myocardium with a conductive metallic coil (titanium, stainless steel, other conductive alloys) or any other conductive anchor (hooks, barbs, arms), and charged and controlled using ultrasonic communication and energy. The RPWs are able to communicate with each other to provide Cardiac Resynchronization Therapy (CRT) while in parallel storing energy for continued pacing for several hours or days using a capacitor bank. In this embodiment even in absence of the ultrasonic link to the control node a patient is given enough time to reach a hospital (safety feature) compared to current wired technology that immediately loses pacing capabilities after lead failure. In a preferred embodiment super-capacitor energy storing bank (2 or more capacitors) and rectifying circuit are used to have redundancy in a zero failure environment. One capacitor 503 will be dedicated to pacing and the other 504 will always be fully charged (safety). Although in some exemplary embodiments pressure sensors (MEMs or non-MEMs) may require separate implants, in an exemplary embodiment a MEMS pressure sensor 501 is integrated into the RPWs to actively monitor left and right ventricular pressures. The core unit can include a FPGA 204, a MCU 203 or an ASICs or any combination thereof. In a preferred embodiment a FPGA is used to drive the logic of the MEMs pressure sensor and control all functions within RPW lead in combination with the MCU 203. The electric sensor 502 is used to track real time the electrical behavior of the implant site in order to respond to changes in the rhythm of the heart. These responses from the RWP to changes in the rhythm of the heart can occur in a closed loop with its own core unit, or in a closed loop combination with data provide by the pressure sensor on any of the other of the implants. Pacing responses can also be re-programmed by a clinician on site or remotely using the ERC patch 402.

In a preferred embodiment, the pacing electronics will be encased within a Polyether ether ketone (PEEK) casing and wrapped with medical-grade porous Dacron cloth to promote rapid tissue in-growth reducing thrombogenic risk. In exemplary embodiments the casing can be constructed of other polymers or metals, and may include a non-thrombogenic surface. In an exemplary embodiments the casing will have a single silicone (or other polymer) window above and in contact with the MEMS pressure sensor in order to transmit the external pressure to the sensor without or with reduced interference from the case itself.

Rechargeable system (RS) control node 401 consist of a reprogrammable controller that can coordinate and re-program other implantable elements of the network through the ultrasonic interface, the basic architecture is that shown in FIG. 3 but doesn't include a functional unit 307 since this node doesn't require any sensory or actuator functionalities. The controller is also able to transmit energy from its position just below the skin to other elements implanted further away from the surface. The battery of the controller is recharged through the skin using ultrasonic power transmission, therefore requiring and EMU 300 with harvesting capabilities. The controller will also be reprogrammed/controlled from outside the body and serve as an interface for off-site remote monitoring. The basic architecture of the controller includes multidirectional ultrasonic transducers and a high-capacity rechargeable battery. In an exemplary embodiment a single omnidirectional ultrasonic transducer may be used. In a preferred embodiment two transducers may be used, one directed at the RWP nodes 400 and another toward the skin to communicate with the ERC patch 402.

External recharging and communication (ERC) 402 node/patch will recharge the RS control node through ultrasonic transcutaneous energy transfer when needed, and act as gateway to interconnect the intra-body network to the Internet. This energy transmission/gateway node is external element (wearable) to be used when needed to recharge or reprogram the network. The ERC node/patch has the same primary components as the IoMT platform shown in FIG. 2 with the addition of a functional unit to interphase with the internet or internet of things through WiFi and or Bluetooth BLE. In an Exemplary embodiment the ERC node can be recharged wirelessly, although in a preferred embodiment the ERC node will have a connector port to hookup a recharging cable that can be plugged to the wall. In some exemplary embodiments the ERC node may also have a USB port or Ethernet cable connection slot so that it can be updated or directly connected to a wired modem.

In exemplary embodiments the bi-ventricular pacing network shown in FIG. 4 will be capable of demand pacing and/or rate-responsive pacing. When in demand mode the RWP nodes will monitor the patient's heart rhythm and send electrical pulses if heart rates drops below a predetermined threshold. When in rate-responsive mode the RWP nodes will speed up or slow down your heart rate by sending pacing pulses depending on how active the patient is. In exemplary embodiments of rate-responsive pacing, the elements of the network will monitor other variables of your activity level through sensors in the RWP nodes and RS controller. These additional sensor units will monitor breathing through motion detectors or accelerometer, blood temperature through sensors in the RWP nodes, and other factors independently or as a group, that drive pacing algorithms Such algorithms will work in a closed loop within the intra-body network and should not require physician input during real time implementation.

In another preferred embodiment of UsWB enabled pacing/stimulation networks, ultrasonic energy transfer and communication technologies can be used to reduce complications associated with wired pacing leads (infection, lead failure, pain, etc), reduce battery exchange rates, and hospital visits through remote monitoring in patients who need Neuromodulation/neurostimulation therapies. As shown in FIG. 6, many different pathologies may be treated using neurostimulation or neuromodulation both in the central and peripheral nervous systems. In a preferred embodiment a network of wireless leads nodes, controller node, and external network energy transfer/gateway node, can be used to treat tremors in the Parkinson's disease population through deep brain stimulation (DBS). Similar to the bi-ventricular pacing network the DBS wireless network shown in FIG. 7. consists of three main types of components/nodes (1) reprogrammable stimulation nodes (RSN) 700, (2) rechargeable system (RS) control node 701, and (3) external recharging and communications (ERC) node 702. The ERC node/patch and the RS control node have the same architecture as that described above for the bi-ventricular pacing network, with basic differences in the energy storage/transfer capacity for these two nodes. For the DBS network, the RS control node is implanted in subcutaneous pockets in either the chest of the patient, the back near the neck between the shoulderblades or subcutaneously in the back of the head. ERC node for this DBS network is a wearable that is in contract with the skin as required. During its function it will be located externally on the skin just above the RS control pocket. The ERC node is removable and in preferred embodiments will be attached to the skin using a glued patch. The contract area between the ERC node casing and the skin has ultrasonic coupling material.

As shown in FIG. 8. the components of the RSN nodes are similar to those of the generic functional node described in FIG. 3 with the addition of two functional units, an electrical sensor unit 800 and stimulation unit 801 for multi-contact stimulation. The RSN nodes have reprogrammable electronic hardware that can be easily adapted to unilaterally or bilaterally stimulate the subthalamic nucleus (STN) and/or other structures. The nodes are anchored in the brain and use one or more conductive (metallic) electrode ring contact points. In a preferred embodiment 4 to 8 contact electrode rings are used per RSN node. In a preferred embodiment these ring are made of a platinum Iridium alloy. The RNS node is recharged using ultrasonic waves and therefore include the EMU 802 with harvesting capabilities. RNS nodes 700 have reprogrammable electronic hardware that can be easily adapted to deep brain stimulation or other types of neurostimulation. The RNS nodes are able to communicate with each other to provide bilateral DBS while in parallel storing energy for continued stimulation for several hours using a capacitor 803. In some exemplary embodiments the RNS node will not need long term energy storage (capacitor or battery) as it may use directly the energy being transmitted to it with just transient energy buffering. In a preferred embodiment, energy long-term storage or transient energy buffering need a rectifying circuit 804 to convert AC voltage from the transducer to circuit usable DC voltage. The core unit 805 will include a FPGA, a MCU or an ASICs or any combination thereof. In a preferred embodiment a FPGA is used to control all functions within RNS node in combination with the MCU. The electric sensor 800 is used to track real time the electrical behavior of the implant site in order to respond to abnormal firing of neurons directly associated to tremors. The stimulation ring array 801 will emit electrical signals (square wave, sinusoidal wave, or other wave geometries) with frequencies between 3-250 Hz (mode dependent) to mitigate tremors in the patient. The processing, communication, and rapid response capabilities of the RNS nodes also allow the system to sense from the electrode rings and then alter the stimulation output based upon that input—a so-called "closed-loop" system, which is the basis for a new technology paradigm in DBS. Although unidirectional ultrasonic transducers may be used; in preferred embodiments Semi-spherical piezo electric transducers and/or omni-directional piezoelectric transducers are used by the RNS nodes to reduce directional sensitivity when emitting or receiving the ultrasonic waves. The casing is constructed of electric insulating materials, in a preferred embodiment the casing will be constructed of polyurethane. Use of a single RNS node in the network allow for unilateral stimulation while two RNS nodes are used for bilateral stimulation. DBS sites in which the RNS transducers can be used include the subthalamic nucleus, globus pallidus internus, pedunculopontine nucleus, and ventral intermediate nucleus of the thalamus among others.

In an exemplary embodiment of wireless UsWB treatment networks, elements from the bi-ventricular cardiac pacing network and the DBS network can be combined to help patients with heart failure (HF). Recent declines in mortality of HF patients have been attributed to the use of cardiac resynchronization therapy (CRT). Studies have also shown that remote monitoring of cardiac implantable electronic devices improves HF patient survival and is also associated with reductions in hospitalization and health care costs. CRT combined with inotropes has been shown to improve heart function leading to reduced mortality. Neurostimulation of the sympathetic and parasympathetic nerves can control stroke volume (sympathetic to increase, parasympathetic to decrease contraction), thus provide similar mechanistic results as the use of inotropes. Therefore, clinical evidence suggests that an intelligent CRT device that can be monitored and reprogramed remotely, and that can be combined with neuromodulation to improve heart function would have a profound impact on treatment of HF patients.

A modular neuromodulation/CRT network with pressure monitoring capabilities will not only improve patient outcomes but also reduce hospitalization rates and healthcare economics. The primary elements of the network for treatment of HF in patients through pacing/neuromodulation, as illustrated in FIG. 9, are: (i) Reprogrammable cardiac wireless pacing (RCWP) node 900; (ii) reprogrammable neuro wireless pacing (RNWP) node 901; (iii) vascular pressure monitoring (VPM) node; (iv) rechargeable system (RS) control node; and (v) external recharging and communication (ERC) node. All the elements in this network communicate through the Ultrasonic WideBand (UsWB) technology; and are recharged using ultrasonic energy transmission (excluding recharging of the ERC node).

The ERC node and the RS control node have the same architecture as that described above for the bi-ventricular pacing network and DBS network, with basic differences in the energy storage and transfer capacity of these two nodes. For the neuromodulation/CRT network, the RS controller is implanted in subcutaneous pockets in either the chest of the patient. In an exemplary embodiment, a second RS controller may be required in the network if the distance between the RCWP and RNWP is too long and requires a network bridge. Since the RS control node in this network is required to communicate with the RCWP nodes, the RNWP nodes, and the ERC patch, several ultrasonic transducers are required. These transducers may be unidirectional, multidirectional or omnidirectional as required by implant location geometry. ERC node/patch for this DBS network is a wearable which is in contact with the skin that during its function will be located externally on the skin just above the RS control pocket. The ERC patch is removable and in preferred embodiments is attached to the skin using a glued patch. The contract area between the ERC node casing and the skin has ultrasonic coupling material.

Figure 10A:
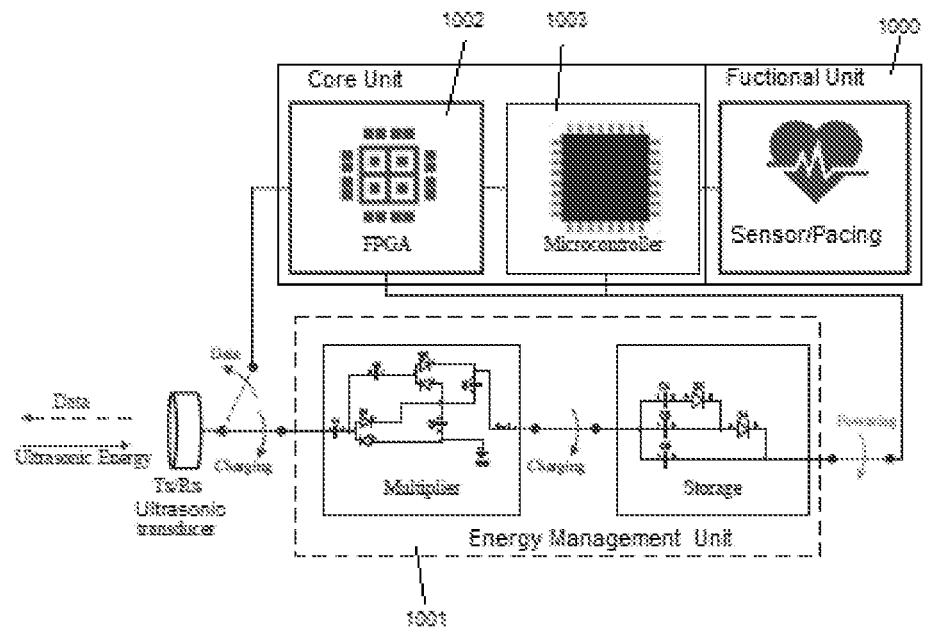

As shown in FIG. 10A. Reprogrammable wireless pacing (RCWP) nodes architecture is similar to those of the generic functional node described in FIG. 3 with and additional electric sensing and pacing functional units 1000. The RCWP nodes are recharged using ultrasonic waves and therefore include the EMU 1001 with harvesting capabilities. Reprogrammable wireless pacing RCWP nodes 900 have reprogrammable electronic hardware and are anchored to the myocardium with a conductive metallic coil 905 (titanium, Stainless Steel, Other conductive alloys) or any other conductive anchor (hooks, barbs, arms), and are controlled using UsWB. The RCPWs are able to communicate with each other to provide CRT while in parallel storing energy for continued pacing for several hours or days using a single capacitor or capacitor bank. In a preferred embodiment, even in absence of the ultrasonic link to the RS control node, a patient is given enough time to reach a hospital (safety feature). In a preferred embodiment, a capacitor energy storing bank (2 or more capacitors) and rectifying circuit are used to have redundancy in a zero failure environment. The core unit can include a FPGA 1002, a MCU 1003 or an ASICs or any combination thereof. In a preferred embodiment a FPGA is used to control all functions within RCPW node in combination with the MCU. The electric sensor 1000 is used to track real time the electrical behavior (EKG) of the implant site in order to respond to changes in the rhythm of the heart. These responses from the RWP to changes in the rhythm of the heart can occur in a closed loop with its own core unit, or in a closed loop combination with data provide by the VPM node or any of the other network elements. Pacing responses can also be re-programmed by a clinician on site or remotely using the ERC node 903. In a preferred embodiment the pacing electronics will be encased within a Polyether ether ketone (PEEK) casing and wrapped with medical-grade porous Dacron cloth to promote rapid tissue in-growth reducing thrombogenic risk. In exemplary embodiments the casing can be constructed of other polymers or metals, and may include a non-thrombogenic surface.

Figure 10B:
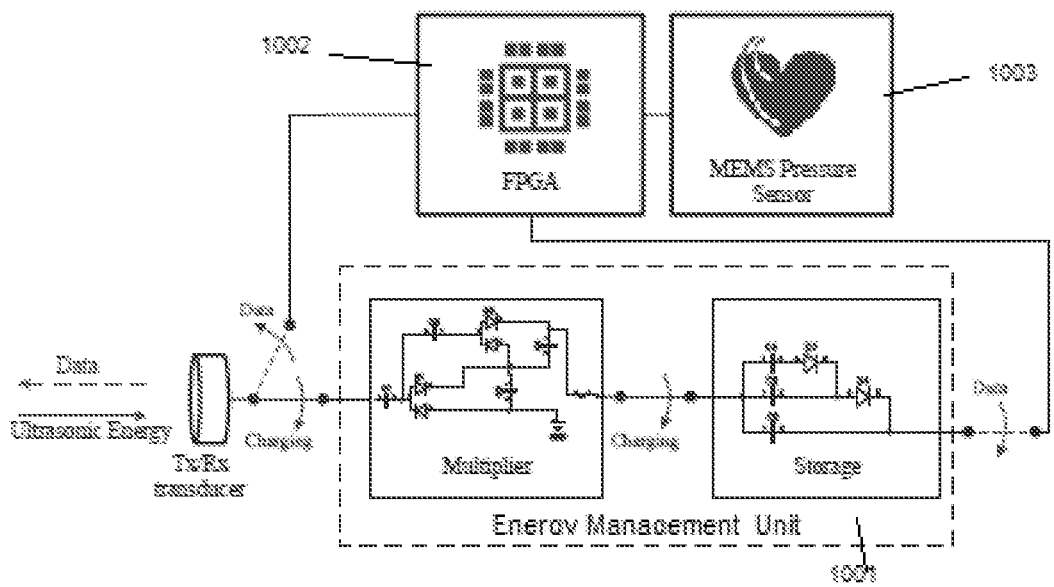

As shown in FIG. 10b, the vascular pressure monitor (VPM) node is a discrete implant in the neuromodulation/CRT network. The core unit for the VPM node may include a FPGA 1002, and/or MCU and/or ASICs. In a preferred embodiment the core unit only includes a FPGA 1002 in order to reduce implant size. The VPM node is recharged using ultrasonic waves and therefore include the EMU 1001. The ultrasonic interface of the IoMT platform, together with the energy management unit (Energy harvesting unit and capacitor-based energy storage) allows for wireless node function. In a preferred embodiment only transient energy storage (small capacitor or energy buffer) is required. Ultrasonic powering and communication capabilities are connected to a pressure sensor, in a preferred embodiment a MEMs pressure sensor is used. The VPN node uses a polymeric or resin casing to isolate the electronics from contacting blood. In a preferred embodiment, non-thrombogenic surfaces are used on the external faces of the casing. In an exemplary embodiment a window of elastomeric, linear elastic and or thinned out polymer is used to transfer the pressure load from the fluid to the MEMs sensor. Many exemplary embodiments can use, hooks, rods, suture, coils, arms, cylindrical stents among other as anchoring elements. In a preferred embodiment, a self-expanding Nitinol anchor wire is used to attach the VPN node to the pulmonary artery 906. The VPN node will be deliver to its implant site using catheter based endovascular methods.

The components of the RNWP nodes are similar to those of the generic functional node described in FIG. 3 with the addition of two functional units, an electrical sensor unit and stimulation unit for single contact and/or multi-contact stimulation. The RNWP nodes have reprogrammable electronic hardware that can be easily adapted for unilateral or bilateral (multipoint) stimulation of sympathetic and parasympathetic nerves at the carotid level. The nodes are anchored to the carotid nerves and use one or more conductive (metallic) electrode ring contact points located on the inner surface of the anchoring collar 907. In a preferred embodiment these rings are made of a platinum Iridium alloy. The RNWP nodes are recharged using ultrasonic waves and therefore include the energy management unit with harvesting capabilities. The RNWP nodes are able to communicate with each other to provide bilateral carotid nerve stimulation while in parallel storing energy for continued stimulation for several hours/days using a capacitor or capacitor bank. In a preferred embodiment energy storage elements need a rectifying circuit 804 to convert AC voltage from the transducer to circuit usable DC voltage. The core unit will include a FPGA a MCU or an ASICs or any combination thereof. In a preferred embodiment a FPGA is used to control all functions within RNWP nodes in combination with the MCU. The electric sensor is used to track real time the electrical behavior of the implant site in order to stimulate at different frequencies and times the parasympathetic and sympathetic nerves to increase or decrease heart contractility/stroke volume. The stimulation ring array will emit electrical signals (square wave, sinusoidal wave, or other wave geometries) to change contractility of the heart/stroke volume. The processing, communication, and rapid response capabilities of the RNWP nodes also allow the system to sense from the electrode rings and then alter the stimulation output based upon that input—a so-called "closed-loop" system. Although unidirectional transducers may be used, in preferred embodiments multidirectional transducers, semi-spherical piezo electric transducers and/or omni-directional piezoelectric transducers are used by the RNWP nodes to reduce directional sensitivity. The casing is constructed of electric insulating materials, in a preferred embodiment the casing will be constructed of a polymer or resin.

The RS control node will coordinate CRT with neuromodulation to ensure synchronized changes in heart rate and contraction. Interaction with the VPM node will allow to improve therapy according to changes in hemodynamics. Use of the ERC node to send pacing, neuromodulation, and vascular pressure data remotely will allow clinicians to closely monitor patients reducing the need on in-hospital visits.

It is to be understood that the above-described devices and methods for treatment of patients using ultrasonic wireless networks of implantable and non-implantable devices may include additional or alternative steps and aspects, based on the foregoing description relating to the various nodes/devices and tools described herein. Accordingly, as a result of the structure and functionality of the above-described networks, devices/nodes and tools, one skilled in the art would appreciate the different methods in which they may be utilized.

Many modifications and other embodiments of the present invention will come to mind to one skilled in the art to which the invention pertains upon having the benefit of the teachings presented herein through the foregoing descriptions and the associated drawings. Therefore, it is to be understood that the present invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A wireless medical device network comprising:
a plurality of networked elements comprising at least two nodes of an intra-body network, wherein:
a first node is configured to be connected to the nervous system; and
a second node is configured to be implanted within an organ;
wherein the at least two nodes communicate with each other by sending or receiving data using ultrasonic waves; and
wherein the communication between the at least two nodes is effective to coordinate at least one function of the nervous system and/or the organ.

2. The network in claim 1, wherein the ultrasonic wave is a pulsed wave.

3. The network in claim 2, wherein data is encoded in the relative position of ultrasound pulses with respect to a reference.

4. The network in claim 2, wherein data is encoded using a time-hopping scheme in the ultrasonic pulses.

5. The network in claim 2, wherein a single bit of data is encoded in a single ultrasonic pulse.

6. The network in claim 2, wherein a single bit of data is encoded in multiple ultrasonic pulses.

7. The network in claim 2, wherein at least one of the elements can communicate wirelessly to the internet.

8. The network in claim 1, wherein the ultrasonic wave is a continuous wave.

9. The network in claim 1, wherein data is encoded in the frequency domain of the ultrasonic wave.

10. The network in claim 1, wherein data is encoded in the phase domain of the ultrasonic wave.

11. The network in claim 1, wherein data is encoded in the amplitude domain of the ultrasonic wave.

12. The network in claim 1, wherein the ultrasonic wave is generated by a unidirectional ultrasonic transducer.

13. The network in claim 12, wherein the at least two nodes process pacing algorithms in a closed-loop functional network.

14. The network in claim 12, wherein the plurality of networked elements further comprises a rechargeable system (RS) control node, which is configured to coordinate Cardiac Resynchronization Therapy (CRT) with neuromodulation to ensure synchronized changes in heart rate and contraction.

15. The network in claim 1, wherein the ultrasonic wave is generated by a multidirectional ultrasonic transducer.

16. The network in claim 1, wherein at least one of the at least two nodes is wirelessly recharged using ultrasonic waves.

17. A cardiac medical device wireless network comprising the network of claim 1, wherein the second node is configured to be implanted within the heart.

18. The network in claim 17, wherein the second node is used for pacing of a heart chamber.

19. The network in claim 18, wherein at least one control node is used to control a pacing element.

20. The network in claim 18, wherein at least one control node is used to wirelessly recharge the second node using ultrasonic waves.

21. The network in claim 17, wherein the second node has the capacity to measure blood pressure.

22. A neurostimulation medical device wireless network comprising the network of claim 1, wherein the first node is configured to
stimulate or modulate the nervous system.

23. The network in claim 22, wherein the first node is connected to the peripheral nervous system.

24. The network in claim 23, wherein the second node is configured to be implanted within the heart, such that the at least nodes can increase or decrease cardiac function.

25. The network in claim 1, wherein the first node is configured to be implanted within the brain.

26. The network in claim 25, wherein the first node is used for deep brain stimulation therapy.

27. The network in claim 1, wherein each of the at least two nodes comprise a core unit comprising a microcontroller, wherein the core unit further comprises application-specific integrated circuits (ASICs).

28. The network in claim 1, wherein the at least two nodes are configured to combine cardiac resynchronization therapy with neurostimulation.

* * * * *